(12) United States Patent
Paterek

(10) Patent No.: US 7,083,956 B2
(45) Date of Patent: *Aug. 1, 2006

(54) METHOD FOR HYDROGEN PRODUCTION FROM ORGANIC WASTES USING A TWO-PHASE BIOREACTOR SYSTEM

(75) Inventor: James Robert Paterek, Naperville, IL (US)

(73) Assignee: Gas Technology Institute, Des Plaines, IL (US)

( * ) Notice: Subject to any disclaimer, the term of this patent is extended or adjusted under 35 U.S.C. 154(b) by 419 days.

This patent is subject to a terminal disclaimer.

(21) Appl. No.: 10/614,609

(22) Filed: Jul. 7, 2003

(65) Prior Publication Data

US 2005/0009159 A1    Jan. 13, 2005

(51) Int. Cl.
*C12P 3/00* (2006.01)
*C12P 1/04* (2006.01)

(52) U.S. Cl. ........................ 435/168; 435/170; 435/262

(58) Field of Classification Search ................... None
See application file for complete search history.

(56) References Cited

U.S. PATENT DOCUMENTS

| | | | |
|---|---|---|---|
| 4,022,665 A | 5/1977 | Ghosh et al. | |
| 4,052,173 A * | 10/1977 | Schulz | 48/202 |
| 4,268,279 A | 5/1981 | Shindo et al. | |
| 4,316,961 A | 2/1982 | Klass et al. | |
| 4,318,993 A | 3/1982 | Ghosh et al. | |
| 4,329,428 A | 5/1982 | Ghosh et al. | |
| 4,424,064 A | 1/1984 | Klass et al. | |
| 4,468,463 A * | 8/1984 | Arsovic | 435/290.4 |
| 4,696,746 A | 9/1987 | Ghosh et al. | |
| 4,735,724 A | 4/1988 | Chynoweth et al. | |
| 4,966,699 A | 10/1990 | Sasaki et al. | |
| 5,198,110 A | 3/1993 | Hanai et al. | |
| 5,500,123 A | 3/1996 | Srivastava | |
| 5,693,230 A | 12/1997 | Asher | |
| 5,760,257 A * | 6/1998 | Tanaka et al. | 554/36 |
| 5,782,950 A * | 7/1998 | Kanitz et al. | 71/10 |
| 5,821,111 A * | 10/1998 | Grady et al. | 435/252.5 |
| 6,342,378 B1 * | 1/2002 | Zhang et al. | 435/168 |
| 6,887,692 B1 * | 5/2005 | Paterek | 435/168 |

* cited by examiner

*Primary Examiner*—David M. Naff
*Assistant Examiner*—Deborah K. Ware
(74) *Attorney, Agent, or Firm*—Mark E. Fejer

(57) ABSTRACT

A method and system for hydrogen production in which a feedstock of at least one biodegradable solid is introduced into a first stage anaerobic bioreactor and a liquid effluent formed. The liquid effluent is transferred into a second stage anaerobic bioreactor having a plurality of hollow semipermeable fibers having an outer surface coated with a biofilm formed by at least one hydrogenogenic bacteria, which forms hydrogen gas within the lumen of the hollow semipermeable fibers. The hydrogen thus produced is removed from the lumen of the hollow semipermeable fibers.

9 Claims, 5 Drawing Sheets

METHOD FOR HYDROGEN PRODUCTION FROM ORGANIC WASTES USING A TWO-PHASE BIOREACTOR SYSTEM

BACKGROUND OF THE INVENTION

1. Field of the Invention

This invention relates to two-phase anaerobic digestion of biodegradable feedstocks, such as organic wastes and manure. More particularly, this invention relates to a method and apparatus for two-phase anaerobic digestion of organic wastes, such as manure from large animal production, food processing wastes, as well as energy crops, e.g. grasses, corn etc. for producing hydrogen gas for use in energy production in which the second anaerobic digestion phase is carried out in a bioreactor vessel utilizing hollow semipermeable fibers in which the liquid effluent from the first anaerobic digestion phase is transmitted into the second anaerobic digestion liquid phase and processed by hydrogenogenic cultures present in this liquid phase disposed on the outer surfaces of the hollow semipermeable fibers. The fibers are operated at a mild vacuum (about 15–20 mm $H_2O$). The hydrogen gas generated by the hydrogenogenic cultures is passed through the semipermeable walls of the hollow semipermeable fibers and into the fiber lumen from which it is then removed. The hydrogen gas generated can be used in conjunction with fuel cell technology to generate electricity on the farms and factories producing the wastes, to replace or supplement the needs of the facilities.

The high-organic wastes generated by these farms and factories are now a liability for them and in many cases incur a cost for disposal. In the case of farms and large animal production facilities, the wastes are discharged to a lagoon for anaerobic digestion to proceed until land application is executed. However, lagoons release a number of gases, including greenhouse gases, methane and carbon dioxide to the atmosphere, which increases their negative impact to the environment. This invention converts this liability into an asset.

2. Description of Related Art

The production of methane and other usable gases by anaerobic digestion of various organic wastes is well-known. The organic feed mixture which provides the substrate for anaerobic biodegradation may comprise a wide variety of organic carbon sources, ranging from raw sewage sludge to municipal refuse, or biomass material such as plants and crop wastes. Anaerobic digestion of organic feedstocks generally involves hydrolysis fermentation of organic feedstocks to acidic intermediates by acid forming bacteria and conversion of the acidic intermediates to useful gases, such as methane, by methane-producing organisms. Many digester designs, feedstocks mixtures and additives have been proposed to increase the methane yield from anaerobic digestion and to provide greater conversion efficiency of organic materials to useful products.

Early designs of sewage digesters attempted to biodegrade sewage sludge for the purposes of sludge volume and odor reduction in an unmixed digester, but they were generally unsuccessful because they failed to provide adequate control of solids inventory, and they developed serious problems such as scum buildup, temperature fluctuations, unequal microbial activity and limited contact between the organic material and the bacteria. Most newer anaerobic digesters for biological conversion of biomass and community wastes are continuously stirred tank reactors, which provide complete mixing of the reactor contents. Solids and hydraulic retention times are equal in continuously stirred tank reactors and both hydrolysis fermentation reactions converting organic materials to acidic intermediates and methane-producing reactions converting acidic intermediates to methane and other gases occur throughout the reactors.

Many organic feedstocks have a relatively low suspended solids content, for example less than about 10 percent suspended solids. The high water content of these types of organic feedstocks causes washout of feed solids and microorganisms from continuously stirred tank reactors at high feed loadings due to high dilution rates. Washout of feed solids and microorganisms results in reduced conversion efficiency and unstable digester conditions. Shorter feed solids retention times in the digester, washout of slow-growing methanogenic bacteria and accumulation of inhibitory acidic fermentation products contribute to low conversion efficiency and reduced methane production.

Anaerobic filter-type reactors promote the retention of bacteria in the digester by attaching bacteria to fixed inert materials in the digester. Anaerobic filter-type digesters are limited to primarily liquid feedstocks containing less than about 1 percent solids because they become plugged when solids concentration in the digester increases due to higher solids loading or accumulation of solids over longer periods of operation.

U.S. Pat. No. 4,329,428 teaches production of methane gas in higher yields and at higher rates by thermophilic and mesophilic anaerobic digestion of a mixture of plant material of terrestrial or aquatic origin and organic waste. U.S. Pat. No. 4,424,064 teaches production of methane gas with higher yields and at higher rates by thermophilic or mesophilic anaerobic digestion of aquatic plant material, at least a portion or all of which has been grown in organically polluted water. U.S. Pat. No. 4,316,961 teaches higher yields of methane gas at higher rates by thermophilic or mesophilic anaerobic digestion of plant material and/or organic waste of normally low biodegradability in the presence of an extract of different plant material.

Separated two phase anaerobic digestion processes have been found to enhance the conversion efficiency. See, for example, U.S. Pat. No. 4,318,993. In an acid first phase, the microbial population and operating conditions are selected to promote the conversion of organic carbonaceous matter to volatile fatty acids of low molecular weight. The volatile fatty acids remain solubilized in the liquid portion of the digester contents. The liquid and solid effluent from the acid phase is conveyed to a methane second phase, where methanogenic microorganisms convert the volatile fatty acids to product gas composed primarily of methane and carbon dioxide. Product gas is removed from the methane phase and processed, or scrubbed, to separate the methane component which is drawn off as pipeline gas. U.S. Pat. No. 4,022,665 teaches certain specific operating conditions for a two phase anaerobic digestion process in separated vessels which promotes more efficient conversion of organic material.

The use of hollow semipermeable fibers in connection with the processing and treatment of various liquids is well documented in the prior art. U.S. Pat. No. 4,268,279 teaches microporous hollow fibers with a liquid in the fiber lumen and a fluid outside the fiber allowing gaseous components to transfer through the microporous fiber to the inside or outside of the fiber. U.S. Pat. No. 4,966,699 teaches a hollow fiber membrane fluid processor providing counter current flow of fluid in the fiber lumen and the fluid surrounding the outside of the fibers from one end of the fiber bundle to the other. U.S. Pat. No. 5,198,110 teaches a bundle of permselective hollow fibers having a plurality of filaments extending substantially lengthwise over the length of the exterior of each fiber. U.S. Pat. No. 5,693,230 teaches a hollow fiber contactor and process having forced circulation with entry of fluid to be processed through the open ended lumen of a porous input hollow fiber having its opposite end closed and exit of treated fluid through the open ended lumen of an adjacent or nearby porous output hollow fiber having its opposite end closed. In the contactor, the fluid to be processed passes through the porous wall of an input hollow fiber, contacting a treatment medium and forming a treated fluid which passes through the porous wall of an output hollow fiber and exits the contactor.

SUMMARY OF THE INVENTION

It is one object of this invention to provide a method and system for producing hydrogen from carbonaceous materials such as organic wastes, food processing wastes and energy crops.

It is another object of this invention to provide a method and system using carbonaceous materials for producing hydrogen suitable for direct use in fuel cell applications.

It is another object of this invention to provide a method and system which provides beneficial disposition of the high-organic wastes generated by farms and industry.

These and other objects are addressed by a method for hydrogen production in which a feedstock comprising at least one biodegradable solid is introduced into a first stage anaerobic bioreactor and a liquid effluent formed therein. The liquid effluent is transferred into the body of a second stage anaerobic bioreactor having a plurality of hollow semipermeable fibers. The outer surface of the hollow semipermeable fibers is coated or will become coated with a biofilm comprising at least one hydrogenogenic bacteria, which forms hydrogen which is passed through the semipermeable fiber walls into the hollow semipermeable fibers. The hydrogen is then removed from within the hollow semipermeable fibers, possibly for direct use in a fuel cell application or storage in a hydrogen facility.

The system for producing hydrogen gas in accordance with the method of this invention comprises a first stage anaerobic bioreactor vessel having a feedstock inlet and a liquid effluent outlet and a second stage anaerobic bioreactor vessel having a liquid effluent inlet in fluid communication with the liquid effluent outlet of the first stage anaerobic bioreactor vessel and having a hydrogen gas outlet. A plurality of hollow semipermeable fibers are disposed in the second stage anaerobic bioreactor vessel. The plurality of hollow semipermeable fibers have an outer surface that is coated with a biofilm comprising at least one hydrogenogenic bacteria.

BRIEF DESCRIPTION OF THE DRAWINGS

These and other objects and features of this invention will be better understood from the following detailed description taken in conjunction with the drawings wherein.

DETAILED DESCRIPTION OF THE PRESENTLY PREFERRED EMBODIMENTS

Figure 1:
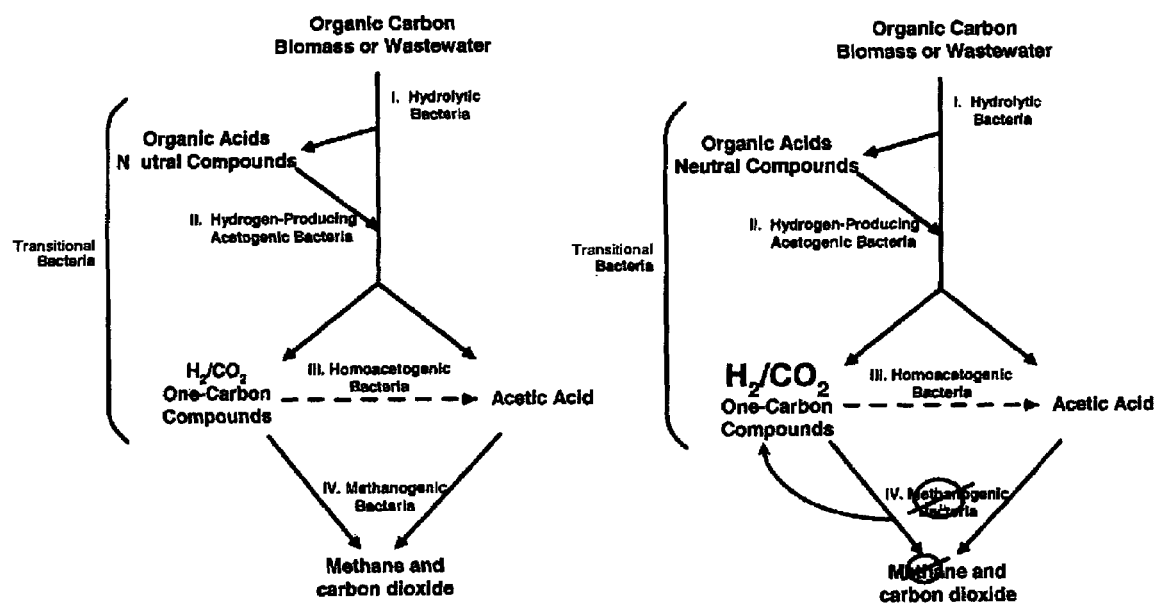
FIG. 1 is a diagram showing the process design and the phenomenon in the second stage anaerobic bioreactor that generates the hydrogen.

This invention involves the use of anaerobic fermentative bacteria that generate hydrogen in the second stage anaerobic bioreactor of a two-stage anaerobic bioreactor system. The fatty acids, such as acetic acids, and other organic fermentation products from the first stage anaerobic bioreactor feed into the area surrounding the hollow semipermeable fibers in the second stage anaerobic bioreactor where it contacts the hydrogenogenic bacteria that form a biofilm on the outer surfaces of the hollow semipermeable fibers. This process slows the production of methane ($CH_4$), but the methanogenic bacteria are inhibited from growth. This may be accomplished by the use of a selective inhibitor of methanogenic bacteria, such as bromoethane sulfonic acid (BES) or by mechanical means, such as maintaining the second stage anaerobic bioreactor at a short hydraulic retention time, typically 1 to 2 days, or by maintaining a pH that is too acidic for the methanogens (<6.8). The two-phase anaerobic bioreactor system of this invention is not limited to the feed source entering the first stage, as long as it can be fermented by associated bacteria, as in the case of manures, or by readily available anaerobic cultures that can digest a range of substrates leading to a range of small organic compounds that the anaerobic hydrogenogenic bacteria use for growth and hydrogen production. FIG. 1 is a diagram illustrative of the phenomenon in the second stage anaerobic bioreactor that generates the hydrogen in accordance with the method of this invention, whereby the formation of methanogenic bacteria is inhibited or suppressed, as a result of which the production of methane, $CH_4$, is suppressed.

Figure 2:
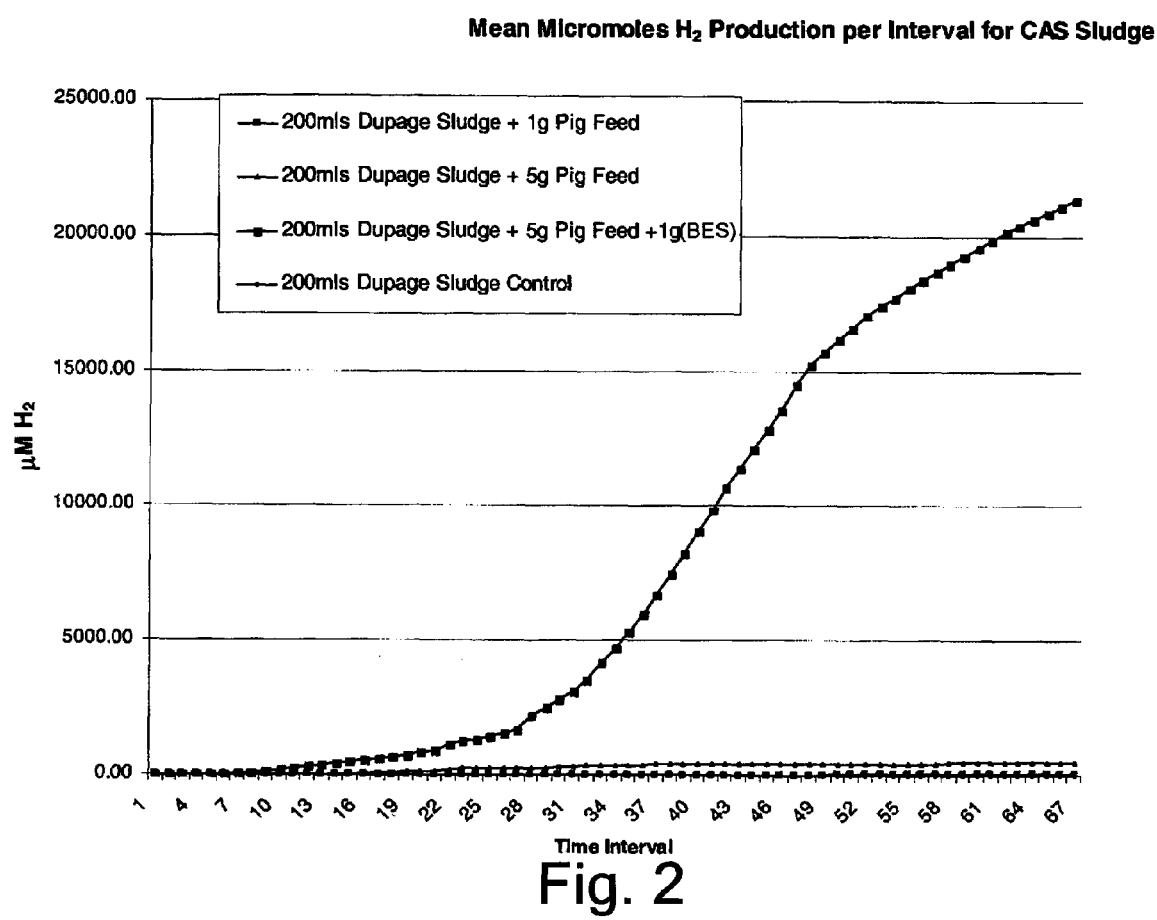
FIG. 2 is a diagram showing the effect on hydrogen production resulting from the use of a methanogenic bacteria selective inhibitor in accordance with one embodiment of this invention.
Figure 3:
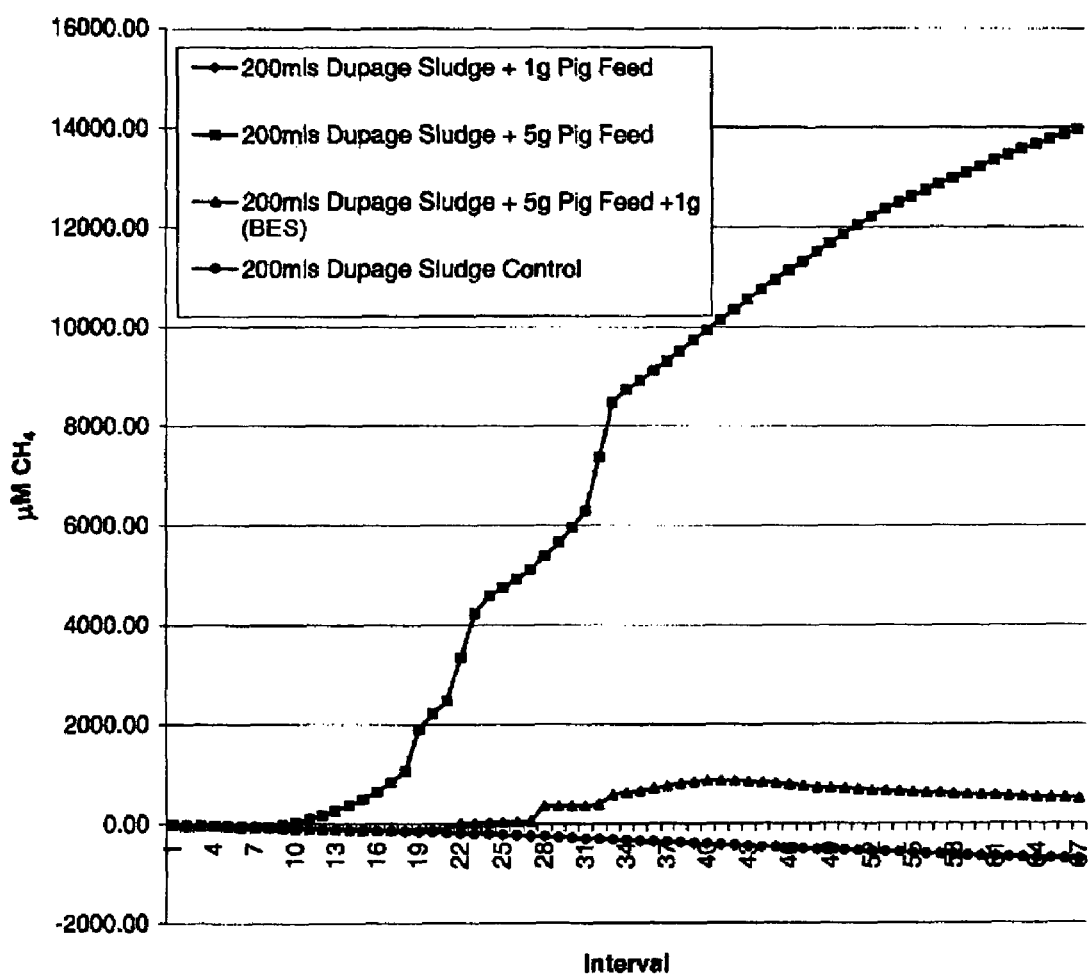
FIG. 3 is a diagram showing the effect on methane production resulting from the use of a methanogenic bacteria selective inhibitor in accordance with one embodiment of this invention.

FIG. 2 shows that the use of a methanogenic bacteria selective inhibitor (BES) results in a substantial increase in hydrogen production compared to systems in which such an inhibitor is not employed. Likewise, FIG. 3 shows that the use of a methanogenic bacteria selective inhibitor substantially reduces the amount of methane produced in accordance with one embodiment of this invention.

Figure 4:
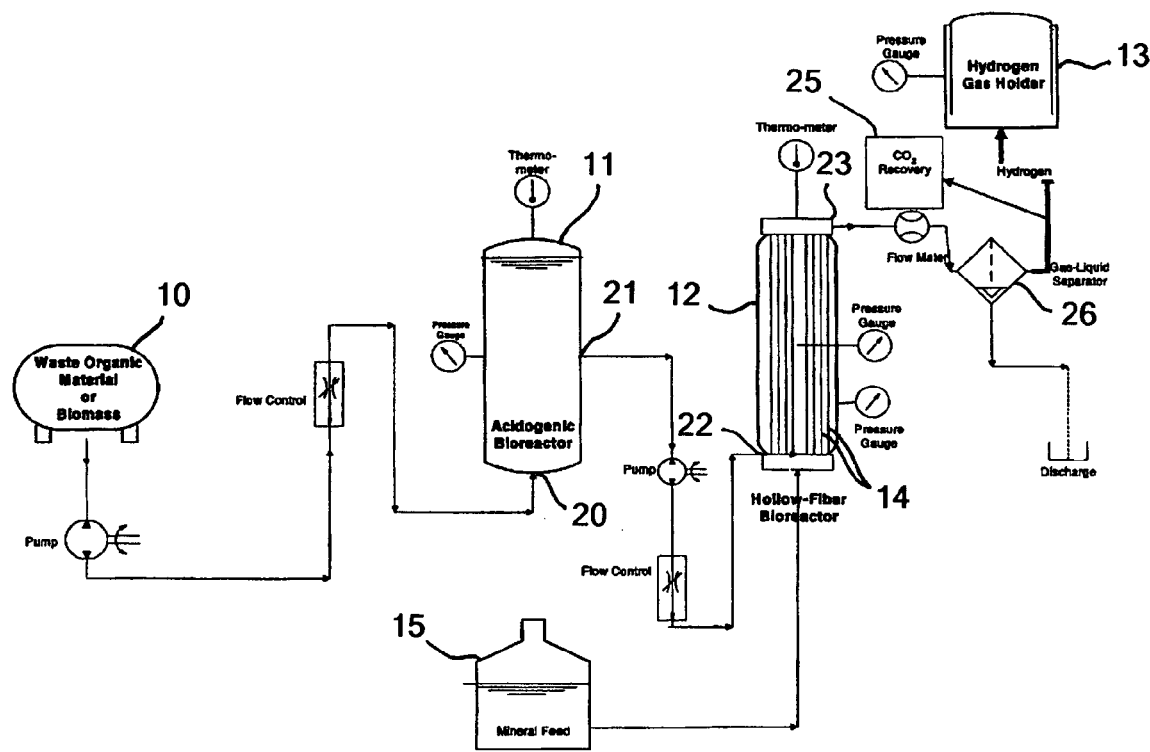
FIG. 4 is a diagram of a two stage anaerobic digestion system for converting organic waste and manures to hydrogen in accordance with one embodiment of this invention.

FIG. 4 is a diagram showing a two-stage anaerobic digestion system for performing the method of this invention. The system comprises a first stage anaerobic bioreactor vessel 11 having a feedstock inlet 20 in fluid communication with a waste organic material and/or biomass source 10 and a liquid effluent outlet 21 in fluid communication with liquid effluent inlet 22 of the second stage anaerobic bioreactor vessel 12. In accordance with one embodiment of this invention, both the first stage anaerobic bioreactor vessel 11 and the second stage anaerobic bioreactor vessel 12 are constantly stirred tank reactors.

Figure 5:
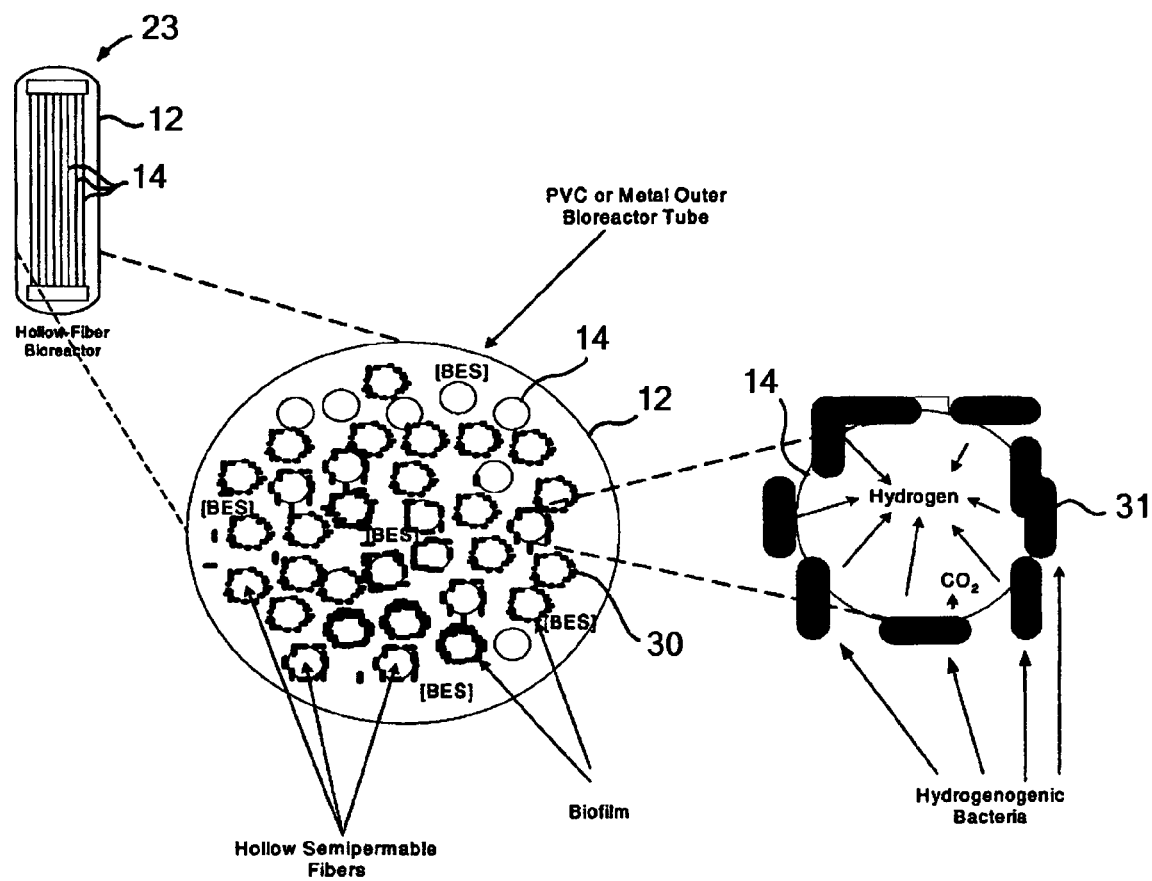
FIG. 5 is a diagrammatic representation of the configuration of the second stage anaerobic bioreactor vessel in accordance with one embodiment of this invention.

Disposed within the second stage anaerobic bioreactor vessel 12 is a plurality of hollow semipermeable fibers 14 arranged to enable liquid effluent entering second stage bioreactor vessel 12 through inlet 22 to surround the hollow semipermeable fibers 14. Disposed within the second stage anaerobic bioreactor vessel 12 in the space surrounding the hollow semipermeable fibers 14 is at least one hydrogenogenic bacterial culture 31 as shown in FIG. 5. During operation of the second stage anaerobic bioreactor in accordance with the method of this invention, the hydrogenogenic bacteria form a biofilm 30 on the outer surfaces of the hollow semipermeable fibers 14. As used herein, the term "hydrogenogenic bacterial culture" refers to a bacterial culture that is suitable for converting the fatty acids and other fermentation products from the first stage anaerobic bioreactor to biomass, hydrogen and, possible $CO_2$. Examples of hydrogenogenic bacteria suitable for use in the method and apparatus include *Bacteroides sp., Clostridium boturicum, Clostridium acetobutylicum, Clostridium perfringeus, Escherichia coli, Enetrobacter aerogenes* or other species of these genera.

Suitable hollow semipermeable fibers for use in this invention have side walls with a viscosity normalized permeance of at least about $10^{-3}$–$10^{-4}$ ft$^2$/sec, preferably greater than about $5\times10^{-3}$ ft$^2$/sec, and most preferably greater than about $5\times10^{-4}$ ft$^2$/sec, and in all cases have pores small enough to prevent the passage of the hydrogenogenic bacteria into the lumen of the fibers. Generally, the thickness of the porous walls of the hollow semipermeable fibers is about 40 to about 60 percent of their outside diameters. The hollow semipermeable fibers may be made of any suitable material which is inert under the conditions of operation of the second stage anaerobic bioreactor, that is not chemically reactive with the liquid effluent or the hydrogenogenic bacteria surrounding the outside of the fibers. Examples of suitable materials include hydrophilic polymeric materials.

Hydrogen is produced in accordance with one embodiment of the method of this invention by introducing a feedstock comprising biodegradable solids into a first stage anaerobic bioreactor vessel 11. Suitable feedstocks include, but are not limited to, manures, food processing wastes, energy crops, such as corn and grasses, and the like. Anaerobic fermentation of the feedstock in the first stage anaerobic bioreactor vessel 11 is carried out under thermophilic conditions, preferably at temperatures in the range of about 45° C. to about 65° C., to kill pathogenic bacteria and protozoa, resulting in the generation of a Class A biosolid (based upon Environmental Protection Agency (EPA) Protocol 503A) that can be land applied or marketed as a soil supplement. To prevent the establishment of methanogenic bacteria, retention times for feedstock within the first stage anaerobic bioreactor should be as short as possible, preferably in the range of about 24 to 48 hours. Alternatively, or in addition thereto, establishment of methanogenic bacteria is further prevented by the addition of a methanogenic bacteria selective chemical inhibitor, such as BES, to the second stage anaerobic bioreactor.

Suitable microorganisms for use in the first stage anaerobic bioreactor are microorganisms that ferment the feedstock to fatty acids and other small carbon compounds. Such microorganisms can be indigenous to the waste, such as manure, or obtained from commercial sources. Examples of such microorganisms include *Clostridium, Bacillus, Bacteroides* and others that generate volatile fatty acids such as acetic, butyric and propionic acids and lactic acid. In accordance with one preferred embodiment of this invention, the first stage anaerobic bioreactor vessel 11 is operated with zero-headspace or near zero-headspace to maintain the gases produced therein ($H_2$, $CO_2$, $H_2S$) in solution for transfer to the hydrogenogenic bacterial biofilm in the second stage hydrogenogenic reactor vessel 12.

The liquid fraction of the effluent from the first stage anaerobic bioreactor vessel 11, which liquid effluent comprises biomass, hydrogen and $CO_2$, is transferred into the second stage anaerobic bioreactor vessel 12 such that contact between the fatty acids, such as acetic and lactic acids, produced in the acidogenic first stage anaerobic bioreactor, and the hydrogenogenic bacterial biofilm is maintained. The hydrogenogenic bacteria utilize the nutrients disposed within the space surrounding the hollow semipermeable fibers for growth and generate hydrogen, which passes through the semipermeable walls of the hollow fibers into the fiber lumen through which it is exhausted from the second stage anaerobic bioreactor. The hydrogenogenic bacteria utilized in the method and system of this invention may be either an axenic culture or a mixed culture.

In accordance with one embodiment of this invention, the hydrogen and $CO_2$ from the second stage anaerobic bioreactor vessel 12 are passed through a gas-liquid separator 21, after which the hydrogen may be collected in a hydrogen gas holder 13 for later use and the $CO_2$ is passed through a $CO_2$ scrubber 25 for recovery of $CO_2$ for possible commercial applications.

In accordance with one embodiment of this invention, if additional complex polymeric carbon compounds disposed in the liquid effluent from the first stage anaerobic bioreactor that could continue to digest in the first stage bioreactor to generate additional fatty acids and other small fermentation products that the hydrogenogenic bacteria can use for growth and/or hydrogen generation remain in the second stage anaerobic bioreactor, such compounds may be recycled to the first stage anaerobic bioreactor for further digestion.

In accordance with one embodiment of this invention, to enable recovery of the biosolids, the biosolids formed in both stages are dewatered.

The benefits of the method and system of this invention will be apparent to those skilled in the art. In particular, the method and system of this invention converts a high percent of organic wastes, such as manures, into hydrogen that can be used in a fuel cell for the generation of electricity. The waste stream is converted without direct release of greenhouse gases, such as methane or carbon dioxide, in the first stage anaerobic bioreactor and the second stage, hydrogenogenic bioreactor. The waste stream from the second stage anaerobic bioreactor generates no methane and a minimal amount of carbon dioxide where a major proportion thereof is trapped in the biomass of the hydrogenogenic bacteria and associated biomass. Hydrogen is generated in the second stage, hydrogenogenic bioreactor by removing hydrogen from the hydrogenogenic consortia before the hydrogen concentration in the liquid effluent reaches levels that inhibit its production, thereby overcoming the need for interspecies hydrogen transfer by methanogenic bacteria or any other hydrogen-consuming microorganisms. The solids generated from both bioreactors meet or exceed the criteria of Class A Biosolids as defined by EPA 503A. And, finally, the second stage anaerobic bioreactor converts the fatty acids and other small fermentation products from the first stage anaerobic bioreactor to biomass and hydrogen and a minimal amount of $CO_2$, which can be captured for commercial uses.

While in the foregoing specification this invention has been described in relation to certain preferred embodiments thereof, and many details have been set forth for purpose of illustration, it will be apparent to those skilled in the art that the invention is susceptible to additional embodiments and that certain of the details described herein can be varied considerably without departing from the basic principles of the invention.

What is claimed is:

1. A method for hydrogen production comprising the steps of:
   introducing a feedstock comprising at least one biodegradable solid into a first stage anaerobic bioreactor and forming a liquid effluent;
   transferring said liquid effluent into a second stage anaerobic bioreactor having a plurality of hollow semipermeable fibers having an outer surface coated with a biofilm comprising at least one hydrogenogenic bacteria, forming hydrogen within lumen of said hollow semipermeable fibers; and
   removing said hydrogen from within said lumen of said hollow semipermeable fibers.

2. A method in accordance with claim 1, wherein said first stage anaerobic bioreactor is operated with substantially zero headspace.

3. A method in accordance with claim 1, wherein a retention time for said feedstock in said first stage anaerobic bioreactor is sufficiently short whereby establishment of methanogenic bacteria in said first stage anaerobic bioreactor is substantially prevented.

4. A method in accordance with claim 1, wherein said first stage anaerobic bioreactor is operated under thermophilic conditions.

5. A method in accordance with claim 4, wherein said first stage anaerobic bioreactor is operated at a temperature in a range of about 45° C. to about 65° C.

6. A method in accordance with claim 1 further comprising adding a methanogenic bacteria specific chemical inhibitor to said second stage anaerobic bioreactor.

7. A method in accordance with claim 1, wherein said second stage anaerobic bioreactor is maintained at a hydraulic retention time in a range of about 24 hours to about 48 hours.

8. A method in accordance with claim 1, wherein $CO_2$ is formed in said lumen from which it is transmitted through a $CO_2$ scrubber system whereby said $CO_2$ is recovered.

9. A method in accordance with claim 1, wherein said first stage anaerobic bioreactor generates biosolids.

* * * * *